United States Patent [19]

Kleber et al.

[11] Patent Number: 5,188,819
[45] Date of Patent: Feb. 23, 1993

[54] MANUFACTURE OF ALUMINUM-BASED ANTICARIOGENIC COMPOSITIONS

[75] Inventors: Carl J. Kleber; Mark S. Putt, both of Fort Wayne, Ind.

[73] Assignee: Purdue Research Foundation, West Lafayette, Ind.

[21] Appl. No.: 840,734

[22] Filed: Feb. 21, 1992

[51] Int. Cl.$^5$ ................................................. A61K 7/16
[52] U.S. Cl. ........................................ 424/49; 426/534
[58] Field of Search .............................. 424/49-58; 426/536

[56] References Cited

U.S. PATENT DOCUMENTS

| | | | |
|---|---|---|---|
| 3,095,356 | 6/1963 | Moss | 167/93 |
| 3,864,472 | 2/1975 | Pensak et al. | 424/55 |
| 4,042,680 | 8/1977 | Muhler et al. | 424/55 |
| 4,108,979 | 8/1978 | Muhler et al. | 424/49 |
| 4,108,981 | 8/1978 | Muhler et al. | 424/55 |
| 4,146,605 | 3/1979 | Ritchey | 424/49 |
| 4,153,732 | 5/1979 | Muhler et al. | 426/72 |
| 4,537,778 | 8/1985 | Clipper et al. | 424/53 |
| 4,590,065 | 5/1986 | Piechota et al. | 424/49 |
| 4,645,662 | 2/1987 | Nakashima et al. | 424/52 |
| 4,695,463 | 9/1987 | Yang et al. | 424/440 |
| 4,749,562 | 6/1988 | Lane et al. | 424/49 |
| 4,766,216 | 8/1988 | Wright et al. | 546/7 |
| 4,772,724 | 9/1988 | Wright et al. | 548/403 |
| 4,822,876 | 4/1989 | Wright et al. | 514/819 |
| 4,842,734 | 6/1989 | Wright et al. | 514/191 |
| 4,882,324 | 11/1989 | Wright et al. | 514/191 |
| 4,976,954 | 12/1990 | Kleber et al. | 424/52 |
| 4,992,256 | 2/1991 | Skaggs | 424/49 |
| 5,057,309 | 10/1991 | Hill et al. | 424/49 |
| 5,064,640 | 11/1991 | Kleber et al. | 424/52 |

FOREIGN PATENT DOCUMENTS

| | | |
|---|---|---|
| 829272 | 12/1969 | Canada . |
| 87117706.9 | 4/1988 | European Pat. Off. . |
| 3610M | 11/1965 | France . |
| 200749 | 8/1953 | New Zealand . |
| 2004463 | 4/1979 | United Kingdom . |

OTHER PUBLICATIONS

R. S. Manly and B. G. Bibby, *J. Dent. Res.*, 28:160 (1948), "Substances Capable of Decreasing the Acid Solubility of Tooth Enamel".

Regolati, et al., *Helv. Odont. Acta.* 13:59 (1960), "Effects of Aluminum and Fluoride on Caries, Fluorine Content and Dissolution of Rat Molars".

Kelada, Nabih P., "Electrochemical Characteristics of Free and Complexed Fluorides in Drinking Water and the Effects of Aluminum and Iron on Fluoride Incorporation Into Tooth Enamel", *Univ. Michigan Thesis*, (1972).

Rosenthal, M. W., *Cosmetics: Science and Technology*, 2nd Ed., John Wiley and Sons, Inc., New York, NY 1977, "Mouthwashes", Chapter 15, pp. 533-562.

C. J. Kleber and M. S. Putt, *Clinical Preventable Dentistry*, vol. 6, No. 6, 1984, pp. 14-25, "Aluminum and Dental Caries".

M. S. Putt and C. J. Kleber, *Journal of Dental Research*, Mar. 1985, "Dissolution Studies of Human Enamel Tested with Aluminum Solutions", pp. 437-439.

C. J. Kleber and M. S. Putt, *Journal of Dental Research*, Dec. 1985, "Uptake and Retention of Aluminum by Dental Enamel", pp. 1374-1376.

M. S. Putt and C. J. Kleber, *Journal of Dental Research*, Nov. 1986, "Effect of pH, Concentration, and Treatment Time of Aluminum Solutions on Acid Dissolution of Enamel", pp. 1356-1358.

D. E. Gerhardt and A. S. Windeler, *Journal of Dental Research*, May-Jun. 1972, vol. 51, No. 3, "Fluoride Uptake in Natural Tooth Surfaces Pretreated with Aluminum Nitrate", p. 870.

H. D. McCann, *Archs. Oral Biol.*, vol. 14, "The Effect of Fluoride Complex Formation On Fluoride Uptake and Retention In Human Enamel", pp. 521-531, 1969.

*Primary Examiner*—Shep K. Rose
*Attorney, Agent, or Firm*—Barnes & Thornburg

[57] ABSTRACT

An improved method for manufacturing a palatable, aluminum-based anticariogenic composition is described. Critical pH adjustment of aluminum salt solutions is accomplished advantageously by pre-blending the aluminum salt solution with at least a portion of a humectant ingredient component. Cellulosic binder components, when used, are preferably hydrated in the pH-adjusted aluminum/humectant solutions. Consistent product rheology and aluminum availability can be obtained in large-scale preparations by blending the aqueous pH-adjusted aluminum/humectant solution with humectant/surfactant and flavor oil/pH-adjusted surfactant premixes.

16 Claims, No Drawings

MANUFACTURE OF ALUMINUM-BASED ANTICARIOGENIC COMPOSITIONS

FIELD OF THE INVENTION

This invention relates to a method for preparing anticariogenic compositions. More particularly, this invention is directed to improvements in the manufacture of aluminum-based anticariogenic compositions.

BACKGROUND AND SUMMARY OF THE INVENTION

Aluminum-based anticariogenic compositions are well known in the art. Yet their preparation presents unique problems not encountered in art-recognized fluoride-based dentifrice and mouthwash formulations. Not only do composition ingredients need to be carefully selected to avoid incompatibility with the active aluminum ion component, but the inherent chemistry of that component itself presents practical formulation problems which have been found particularly difficult to address in large scale preparations of aluminum-based anticariogenic composition for clinical trail.

The source of aluminum ions for aluminum-based anticariogenic compositions are water-soluble aluminum salts which when dissolved in water as the starting point for the preparation of aluminum-based anticariogenic compositions provide a highly acidic solution. The high acidity not only affects composition palatability but can, as well, cause acid-catalyzed degradation of other functional components of the composition. Thus, for example, attempts to hydrate cellulosic binders such as hydroxyethylcellulose in aluminum salt solutions results in some chemical degradation of the binder and concomitant loss of functionality. Likewise, high acidity greatly prolongs the time necessary for binder hydration. Also, the pH of the preparation must be raised above 3.5 to maximize the interaction between the tooth enamel and the aluminum and to prevent acid erosion of the teeth.

Typically the first step in formulation of aluminum ion-based anticariogenic compositions is the preparation of an aluminum salt solution by dissolving the aluminum salt component in a volume of water, preferably a minimum volume of water for a dentifrice. The natural pH levels of such solutions range from about 2.0 to about 4.0. It is critical for product palatability and long term composition stability that the pH of that solution be adjusted by the addition of a food-acceptable base, typically sodium hydroxide, most preferably to a pH of about 3.7 to about 3.9. A significant problem associated with the neutralization process is the hydroxylation of aluminum. Although the hydroxylation of aluminum can be minimized by reducing the rate of pH adjustment (i.e., the rate of base addition) with rapid stirring, the problem is significantly accentuated in large-scale preparations. The aluminum hydroxides precipitated during even carefully controlled base addition will gradually dissolve (assuming the final pH is still less than about 4). However, the time required for that process is not well tolerated; indeed, it is wholly unacceptable in manufacturing operations.

One other problem encountered even in small-scale preparations of aluminum-based anticariogenic compositions derives from the difficulties associated with blending relatively large amounts of surfactants with the aqueous aluminum-containing solution while avoiding excess foaming and mix heterogeneity due to incomplete surfactant dissolution and dilatancy of the binder/abrasive components.

Therefore, it is an object of this invention to provide a process for commercial manufacture of stable, palatable, aluminum-ion based anticariogenic compositions.

Another object of this invention is to provide improvements in the preparation of aluminum-based anticariogenic compositions with consistent aluminum ion activity and composition stability.

It is still another object of this invention to provide an improved, commercially feasible manufacturing process for aluminum-based anticariogenic compositions with the goal of minimizing manufacturing time and assuring composition consistency and quality.

According to the present invention, there is provided an improved method for manufacturing a palatable, aluminum-based anticariogenic composition. One improvement in accordance with this invention derives principally from the discovery that the unwanted precipitation of aluminum hydroxide, during pH adjustment of intermediate aluminum salt solutions can be minimized or even prevented by adding at least a portion of a humectant component of the anticariogenic composition to the aqueous aluminum solution prior to pH adjustment. Further, it has been found that problems associated with cellulosic binder degradation during hydration of the binder in aluminum-ion-containing solutions can be minimized and the hydration process accelerated by carrying out the binder hydration in the aqueous aluminum salt solution after pH adjustment. Finally, it has been found that blending of the critical humectant, surfactant and flavor oil components with the aqueous aluminum salt solution can be facilitated by selective pre-blending of those components. The present invention thus provides for a cost efficient commercially applicable manufacturing process for aluminum-ion-based anticariogenic compositions having consistent physical and chemical (aluminum ion availability) characteristics.

DETAILED DESCRIPTION OF THE INVENTION

This invention is directed particularly to improvements in the manufacture of palatable, aluminum-based anticariogenic compositions. While the present improvements can be adapted to the manufacture of many such aluminum compositions known in the art, they find particular application to the manufacture of aluminum-based anticariogenic compositions comprising a water-soluble aluminum salt, water, humectant, flavor oil, surfactant and sweetener in blended emulsion form. Such compositions are described in detail in U.S. Pat. No. 4,976,954, issued Dec. 11, 1990, the specification of which is specifically incorporated herein by reference.

The improvements in accordance with this invention focus particularly on the preparation/formulation of intermediate premixes of the composition components and the blending of those premixes in formulation of the targeted aluminum-based anticariogenic compositions. Such compositions can take the form of liquids such as a mouthwash formulation or more typically binder/abrasive containing dentifrice gels or pastes.

One aspect of this invention comprises an improved method for preparing a pH-adjusted, aluminum-ion-containing aqueous premix and blending of that source of active aluminum ions with the remaining composition ingredients/excipients. The uniform blending of that aluminum-containing premix with the remaining composition ingredients is facilitated by forming two premixes—one comprising surfactant and humectant components and another comprising a flavor oil and a portion of at least one surfactant component. Blending of the aluminum-ion-containing premix and each of the respective surfactant/humectant and flavor/surfactant premixes are preferably carried out under a vacuum to remove and prevent incorporation of air to the mix. In a preferred embodiment a cellulosic binder is hydrated in the pH-adjusted, aluminum-ion-containing aqueous premix prior to blending with the other premix components. Other binder ingredients and abrasives can be added during the blending operation.

The initial step in carrying out the method of manufacture of this invention comprises the preparation of a pH-adjusted, aluminum-ion-containing aqueous premix. An aluminum salt component is dissolved in a minimum amount of water, typically in a suitable mixer such as a stainless steel Nauta MBX mixer. The source of aluminum ions can be any non-toxic, water-soluble aluminum salt, for example, aluminum potassium sulfate, aluminum chloride, aluminum sodium sulfate, aluminum sodium phosphate, aluminum sulfate, aluminum nitrate, sodium aluminate and mixtures thereof. Aluminum potassium sulfate and aluminum chloride are preferred by reason of their wide availability and established safety. Optionally, a sweetener may be added to the aluminum-ion-containing premix. Typically the sweetener is a non-cariogenic sweetener such as saccharin, cyclamate or aspartame, although sucrose, dextrose, fructose and mixtures thereof can be used.

The pH of the resulting solution of the aluminum salt (again, preferably in a minimum volume of water) is typically about pH 3. To prevent precipitation of aluminum hydroxides during the required pH adjustment, at least a portion of a humectant component of the anticariogenic composition is blended with the aluminum-containing aqueous premix. Typically about 20 to about 80% of the humectant, most preferably about 50% of the humectant component of the anticariogenic composition is added to the aqueous aluminum salt solution prior to pH adjustment. The identity of the humectant is typically dependent on the nature of the targeted anticariogenic composition. In typical paste formulations the humectant is preferably a combination of sorbitol and glycerin, although mannitol, xylitol, propylene glycol and mixtures thereof as well as other edible polyhydric alcohols may also be used. In gel and paste aluminum-based anticariogenic compositions the humectant component typically comprises about 10 to about 40% by weight of the composition.

The addition of humectant to the acidic aqueous salt solution has been found to inhibit the hydroxylation of aluminum upon adjustment of the solution pH by the addition of a food-acceptable base. Thus, for example, sufficient sodium hydroxide solution can be added to the aluminum/humectant solution to adjust the pH from about 3.2 to about 4.0, more preferably about 3.5 to about 3.9, most preferably about 3.7 to about 3.9 rapidly without significant precipitation of aluminum hydroxide. In the absence of added humectant, even a very slow rate of addition of sodium hydroxide to the aluminum salt solution, with rapid stirring, results in precipitation of aluminum hydroxides, an anticariogenically inactive form of aluminum. If the pH is not adjusted too high ($\leq 4$) the precipitated aluminum hydroxide will redissolve slowly into the solution even without added humectant. However, the processing delays appurtenant to aluminum hydroxide precipitation are most desirably avoided in commercial manufacturing processes.

In manufacture of aluminum-based anticariogenic formulations utilizing cellulosic binder components, it has been found in accordance with this invention that the required hydration of such cellulosic binder components, for example, hydroxyethylcellulose, can be carried out advantageously and more rapidly in the pH-adjusted, aluminum-ion-containing premix without acid hydrolysis of the binder and without concomitant impact on the rheological properties of the product composition. Thus, in accordance with one preferred embodiment of this invention in the manufacture of aluminum-based anticariogenic compositions utilizing cellulosic binders, following pH adjustment of the aqueous salt solution premix with sodium hydroxide in the presence of at least a portion of the humectant, a cellulosic binder (for example, hydroxyethylcellulose) can be sifted into the pH-adjusted solution and moderately agitated for about 1 to 2 hours to hydrate the cellulosic binder component. Preferably paste formulations prepared in accordance with the present manufacturing process utilize a combination of hydroxyethylcellulose and silica binders. Silica binders are typically added to the formulation with abrasive components as detailed hereinbelow.

To facilitate blending of surfactant components with the pH-adjusted, aluminum ion/humectant solution, a surfactant/humectant premix (an organic premix) is prepared using the remaining portion of the humectant component and a surfactant component, blending same optionally with organic preservatives, such as parabens, if specified in the anticariogenic composition formulation. The organic premix phase is blended to homogeneity, optionally with heating, to promote the miscibility of the premix components.

Commonly, aluminum-based anticariogenic compositions prepared in accordance with the manufacturing method of the present invention are formulated with multiple surfactants. One preferred surfactant combination is a combination of block copolymers of propylene oxide and ethylene oxide sold under the trade name Pluronics® from BASF Wyandotte Company and polyoxyethylene sorbitan esters sold under the trade name Tween® from Atlas Chemical Industries, Inc. Each of those types of surfactant include multiple surfactant species that can be selected to achieve properties necessary for emulsion stabilization, sudsing capacity, and fine tuning of formulation rheological properties (viscosity, texture, etc.). Thus, for example, preferred paste formulations prepared in accordance with the present invention utilize a combination of Pluronic F127 and Tween 20. The Pluronic F127 imparts good binder qualities, smoothness, consistency and appearance to the paste formulation. Substitution of the Pluronic F87 for all or a portion of the Pluronic F127 component provides a paste with better sudsing functionality.

The surfactant/humectant premix can be prepared by blending at least a portion of the surfactant component, for example, the surfactant component with the higher viscosity where 2 or more surfactants are specified, or with a portion of combined surfactant ingredients. Other organic ingredient components of the anticariogenic formulation can be conveniently blended into the humectant/surfactant premix.

It has also been found that commonly employed flavor oil components are more efficiently blended into the aluminum-ion-based anticariogenic formulations in accordance with this method by preparing a flavor oil/surfactant premix. One preferred surfactant for promoting flavor oil emulsification in the anticariogenic compositions prepared in accordance with this invention are the Tween ® polyoxyethylene derivatives of sorbitan fatty esters, particularly sorbitan monofatty esters, where the ester forming fatty acid is selected from lauric acid, palmitic acid, oleic acid and stearic acid. Another suitable surfactant for pre-blending with flavor oil components to promote stable flavor oil emulsions is sold under the trade name Pluronic L64 ® which contains about 40% hydrophile in the form poly-(oxyethylene) and has a hydrophile/lipophile balance (HLB) of about 15. Many suitable flavoring agents are commercially available including mint, strawberry, menthol, and the like. Flavor oils are typically utilized in amounts ranging from about 0.1% to about 1.5% by weight of the anticariogenic composition.

Preparation of anticariogenic compositions in accordance with this invention is completed by first blending the aqueous aluminum/humectant solution with the humectant/surfactant premix, for example, in a double-planetary mixer equipped with a vacuum hood. The mixture is blended at high speed under a vacuum of, for example, 25 inches of mercury, until a clear mucilage forms. Thereafter inorganic binders and abrasives, for example calcined aluminum silicate, or silica abrasives, each compatible with active aluminum ions in prepared formulations, are preferably first blended in dry powder form and thereafter added to the mucilage with slow stirring until dispersed, after which time the mixer is sealed and operated at high speed under vacuum until the mixture assumes the consistency of a homogenous paste.

Optionally, silica binders can be co-blended with the abrasive component into the formulation. Silica binders cooperate with, for example, cellulosic binder used optionally in the aqueous aluminum/humectant solution to fine tune the rheological properties of the anticariogenic formulations. The preparation of the anticariogenic composition is completed by adding the flavor/surfactant premix to the blended mixture, typically by layering the flavor premix on top of the blended mixture followed by agitating about 15 minutes under a vacuum of about 28 inches of mercury or more, until a uniform-blended composition is produced.

The viscosity, texture, dispersability, sudsing, color and anticariogenic activity of the dentifrice is influenced by the relative proportions of each of the components and in the manner in which they are combined. Tables 1A–1C list formulae of experimental, aluminum-containing dentifrice formulations prepared in accordance with the present invention. Viscosity, pH and ESR data for each of those formulations are reported in Table 2.

TABLE 1A

| DENTIFRICE INGREDIENTS | DENTIFRICE CODES AND COMPOSITIONS (%) | | | | | |
|---|---|---|---|---|---|---|
| | N74P50 | N74P52 | N74P54 | N74P56 | N74P58 | N74P60 |
| Kaopolite 1147 (Kaopolite, Inc.) | 34.02 | 33.00 | 34.00 | 33.00 | 32.00 | 32.00 |
| Zeodent 113 (Huber) | — | — | — | — | — | — |
| Distilled Water | 19.31 | 18.61 | 18.11 | 18.11 | 17.81 | 18.81 |
| Glycerin USP | 14.00 | 17.00 | 16.00 | 17.00 | 16.00 | 16.00 |
| Sorbo (70%) USP | 20.50 | 16.50 | 16.50 | 16.50 | 16.50 | 16.50 |
| Sodium hydroxide (33.3%) | — | — | 0.50 | 0.50 | 0.50 | 0.50 |
| Natrosol 250 MR (Hercules) | 1.50 | 1.50 | 1.50 | 1.50 | 0.50 | 1.00 |
| Zeosyl 200 (Huber) | — | — | — | — | — | — |
| Pluronic F127 (BASF Wyandotte) | 4.00 | 4.00 | 4.00 | 7.60 | 11.50 | 10.00 |
| Pluronic F87 (BASF Wyandotte) | — | — | — | — | — | — |
| Tween 20 (ICI Americas) | 1.80 | 3.60 | — | — | — | — |
| Tween 80 (ICI Americas) | — | — | 3.60 | 1.20 | 0.80 | 0.80 |
| Aluminum potassium sulfate dodecahydrate | 3.54 | 3.54 | 3.54 | 3.54 | 3.54 | 3.54 |
| Dentomint flavor H7703 (Haarman & Reimer) | 0.90 | 1.80 | 1.80 | — | — | — |
| Cassia flavor 1529 (Warner Jenkinson) | — | — | — | 0.60 | 0.40 | 0.40 |
| Colgate flavor S/R 71568 (Felton) | — | — | — | — | — | — |
| Colgate flavor I-1376 (Intarome) | — | — | — | — | — | — |
| Sodium saccharin | 0.25 | 0.25 | 0.25 | 0.25 | 0.25 | 0.25 |
| Methyl paraben | 0.15 | 0.15 | 0.15 | 0.15 | 0.15 | 0.15 |
| Propyl paraben | 0.05 | 0.05 | 0.05 | 0.05 | 0.05 | 0.05 |

| DENTIFRICE INGREDIENTS | DENTIFRICE CODES AND COMPOSITIONS (%) | | | | |
|---|---|---|---|---|---|
| | N74P62 | N74P70 | N74P72 | N74P74 | N74P76 |
| Kaopolite 1147 (Kaopolite, Inc.) | 32.00 | 31.00 | 31.00 | 31.00 | 31.00 |
| Zeodent 113 (Huber) | — | — | — | — | — |
| Distilled Water | 20.31 | 21.81 | 22.81 | 21.01 | 21.01 |
| Glycerin USP | 17.00 | 17.00 | 17.00 | 17.00 | 17.00 |
| Sorbo (70%) USP | 14.00 | 14.00 | 14.00 | 14.00 | 14.00 |
| Sodium hydroxide (33.3%) | 1.20 | 1.00 | — | 1.00 | 1.00 |

TABLE 1A-continued

| | | | | | |
|---|---|---|---|---|---|
| Natrosol 250 MR (Hercules) | 1.00 | 1.00 | 1.00 | 1.00 | 1.00 |
| Zeosyl 200 (Huber) | — | — | — | — | — |
| Pluronic F127 (BASF Wyandotte) | 10.00 | 9.00 | 9.00 | 9.00 | 9.00 |
| Pluronic F87 (BASF Wyandotte) | — | — | — | — | — |
| Tween 20 (ICI Americas) | — | — | — | — | — |
| Tween 80 (ICI Americas) | 0.80 | 0.80 | 0.80 | 0.80 | — |
| Aluminum potassium sulfate dodecahydrate | 3.54 | 3.54 | 3.54 | 3.54 | 3.54 |
| Dentomint flavor H7703 (Haarman & Reimer) | — | — | — | — | — |
| Cassia flavor 1529 (Warner Jenkinson) | 0.40 | 0.40 | 0.40 | — | — |
| Colgate flavor S/R 71568 (Felton) | — | — | — | 1.20 | 2.00 |
| Colgate flavor I-1376 (Intarome) | — | — | — | — | — |
| Sodium saccharin | 0.25 | 0.25 | 0.25 | 0.25 | 0.25 |
| Methyl paraben | 0.15 | 0.15 | 0.15 | 0.15 | 0.15 |
| Propyl paraben | 0.05 | 0.05 | 0.05 | 0.05 | 0.05 |

TABLE 1B

| DENTIFRICE INGREDIENTS | DENTIFRICE CODES AND COMPOSITIONS (%) | | | | | |
|---|---|---|---|---|---|---|
| | N74P78 | N74P80 | N74P86 | N74P88 | N74P90 | N74P92 |
| Kaopolite 1147 (Kaopolite, Inc.) | — | 31.00 | — | — | 30.00 | 30.00 |
| Zeodent 113 (Huber) | 18.00 | — | 18.00 | 20.00 | — | — |
| Distilled Water | 28.31 | 21.01 | 25.31 | 20.81 | 20.81 | 20.81 |
| Glycerin USP | 39.50 | 31.00 | 36.50 | 36.50 | 17.00 | 17.00 |
| Sorbo (70%) USP | — | — | — | — | 13.00 | 13.00 |
| Sodium hydroxide (33.3%) | 1.00 | 1.00 | 1.00 | 1.00 | 1.00 | 1.00 |
| Natrosol 250 MR (Hercules) | 1.00 | 1.00 | 1.00 | 1.50 | — | 0.50 |
| Zeosyl 200 (Huber) | 4.00 | — | 4.00 | 6.00 | 4.00 | 3.50 |
| Pluronic F127 (BASF Wyandotte) | 3.00 | 9.00 | 9.00 | 9.00 | 9.00 | 9.00 |
| Pluronic F87 (BASF Wyandotte) | — | — | — | — | — | — |
| Tween 20 (ICI Americas) | 0.80 | — | 0.80 | 0.80 | 0.80 | 0.80 |
| Tween 80 (ICI Americas) | — | 0.80 | — | — | — | — |
| Aluminum potassium sulfate dodecahydrate | 3.54 | 3.54 | 3.54 | 3.54 | 3.54 | 3.54 |
| Dentomint flavor H7703 (Haarman & Reimer) | — | — | — | — | — | — |
| Cassia flavor 1529 (Warner Jenkinson) | 0.40 | — | 0.40 | 0.40 | 0.40 | 0.40 |
| Colgate flavor S/R 71568 (Felton) | — | 1.20 | — | — | — | — |
| Colgate flavor I-1376 (Intarome) | — | — | — | — | — | — |
| Sodium saccharin | 0.25 | 0.25 | 0.25 | 0.25 | 0.25 | 0.25 |
| Methyl paraben | 0.15 | 0.15 | 0.15 | 0.15 | 0.15 | 0.15 |
| Propyl paraben | 0.05 | 0.05 | 0.05 | 0.05 | 0.05 | 0.05 |

| DENTIFRICE INGREDIENTS | DENTIFRICE CODES AND COMPOSITIONS (%) | | | | |
|---|---|---|---|---|---|
| | N74P94 | N74P96 | N74P98 | N74P100 | N74P108 |
| Kaopolite 1147 (Kaopolite, Inc.) | 30.00 | 29.00 | 34.00 | 31.00 | 31.00 |
| Zeodent 113 (Huber) | — | — | — | — | — |
| Distilled Water | 20.81 | 20.81 | 21.31 | 21.81 | 21.81 |
| Glycerin USP | 17.00 | 17.00 | 17.00 | 17.00 | 17.00 |
| Sorbo (70%) USP | 13.00 | 13.00 | 17.00 | 14.00 | 14.00 |
| Sodium hydroxide (33.3%) | 1.00 | 1.00 | 1.00 | 1.00 | 1.00 |
| Natrosol 250 MR (Hercules) | 0.25 | — | 1.50 | 1.50 | 1.00 |
| Zeosyl 200 (Huber) | 3.75 | 5.00 | — | — | — |
| Pluronic F127 (BASF Wyandotte) | 9.00 | 9.00 | — | — | 6.00 |
| Pluronic F87 (BASF Wyandotte) | — | — | 3.00 | 9.00 | 3.00 |
| Tween 20 | 0.80 | 0.80 | 0.80 | 0.80 | 0.80 |

TABLE 1B-continued

| | | | | | |
|---|---|---|---|---|---|
| (ICI Americas) | | | | | |
| Tween 80 | — | — | — | — | — |
| (ICI Americas) | | | | | |
| Aluminum potassium sulfate dodecahydrate | 3.54 | 3.54 | 3.54 | 3.54 | 3.54 |
| Dentomint flavor H7703 (Haarman & Reimer) | — | — | — | — | — |
| Cassia flavor 1529 (Warner Jenkinson) | 0.40 | 0.40 | 0.40 | 0.40 | 0.40 |
| Colgate flavor S/R 71568 (Felton) | — | — | — | — | — |
| Colgate flavor I-1376 (Intarome) | — | — | — | — | — |
| Sodium saccharin | 0.25 | 0.25 | 0.25 | 0.25 | 0.25 |
| Methyl paraben | 0.15 | 0.15 | 0.15 | 0.15 | 0.15 |
| Propyl paraben | 0.05 | 0.05 | 0.05 | 0.05 | 0.05 |

TABLE 1C

| DENTIFRICE INGREDIENTS | DENTIFRICE CODES AND COMPOSITIONS (%) | | | | | | | | | |
|---|---|---|---|---|---|---|---|---|---|---|
| | N74P110 | N74P112 | N74P114 | N74P118 | N74P120 | N74P122 | N74P126 | N74P145 | N74P146 | N74P147 |
| Kaopolite 1147 (Kaopolite, Inc.) | 31.00 | 28.00 | — | 28.00 | 29.00 | 31.00 | 31.00 | 30.28 | 31.57 | 32.45 |
| Zeodent 113 (Huber) | — | — | 20.00 | — | — | — | — | — | — | — |
| Distilled Water | 21.51 | 22.47 | 20.81 | 22.01 | 21.01 | 23.01 | 23.55 | 21.01 | 21.01 | 21.01 |
| Glycerin USP | 17.00 | 17.00 | 35.70 | 17.00 | 17.00 | 17.00 | 17.00 | 17.00 | 17.00 | 17.00 |
| Sorbo (70%) USP | 14.00 | 14.00 | — | 13.00 | 13.00 | 14.00 | 13.00 | 13.00 | 13.00 | 13.00 |
| Sodium hydroxide (33.3%) | 1.00 | 1.00 | 1.00 | 1.00 | 1.00 | 1.00 | — | 0.60 | 0.40 | 0.20 |
| Natrosol 250 MR (Hercules) | 0.50 | 1.00 | 1.50 | 0.75 | 0.50 | 1.00 | 0.50 | 0.75 | 0.75 | 0.75 |
| Zeosyl 200 (Huber) | — | 4.00 | 6.00 | 3.25 | 3.50 | 4.00 | 3.50 | 3.25 | 3.25 | 3.25 |
| Pluronic F127 (BASF Wyandotte) | 9.00 | — | 9.00 | 9.00 | 9.00 | — | 9.00 | 9.00 | 9.00 | 9.00 |
| Pluronic F87 (BASF Wyandotte) | — | 3.00 | — | — | — | 3.00 | — | — | — | — |
| Tween 20 (ICI Americas) | 0.80 | 0.80 | 0.80 | 0.80 | 0.80 | 0.80 | 0.80 | 0.80 | 0.80 | 0.80 |
| Tween 80 (ICI Americas) | — | — | — | — | — | — | — | — | — | — |
| Aluminum potassium sulfate dodecahydrate | 3.54 | 7.08 | 3.54 | 3.54 | 3.54 | 3.54 | — | 2.66 | 1.77 | 0.89 |
| Dentomint flavor H7703 (Haarman & Reimer) | — | — | — | — | — | — | — | — | — | — |
| Cassia flavor 1529 (Warner Jenkinson) | — | — | — | — | — | — | — | — | — | — |
| Colgate flavor S/R 71568 (Felton) | — | — | — | — | — | — | — | — | — | — |
| Colgate flavor I-1376 (Intarome) | 1.20 | 1.20 | 1.20 | 1.20 | 1.20 | 1.20 | 1.20 | 1.20 | 1.20 | 1.20 |
| Sodium saccharin | 0.25 | 0.25 | 0.25 | 0.25 | 0.25 | 0.25 | 0.25 | 0.25 | 0.25 | 0.25 |
| Methyl paraben | 0.15 | 0.15 | 0.15 | 0.15 | 0.15 | 0.15 | 0.15 | 0.15 | 0.15 | 0.15 |
| Propyl paraben | 0.05 | 0.05 | 0.05 | 0.05 | 0.05 | 0.05 | 0.05 | 0.05 | 0.05 | 0.05 |

TABLE 2

| DENTIFRICE CODE | DENTIFRICE DESCRIPTION | BROOKFIELD VISCOSITY 10 RPM | | DENTIFRICE pH | | ENAMEL SOLUBILITY PHOSPHORUS | | REDUCTION (%)* CALCIUM | |
|---|---|---|---|---|---|---|---|---|---|
| | | | VISUAL | PASTE | SLURRY | 1 PTD | 4 PTD | 1 PTD | 4 PTD |
| N74P50 | 2000 Al/Kaolin | 69 | thick | 3.0 | 3.5 | 83 (6) | 61 (8) | 85 (7) | 69 (16) |
| N74P52 | 2000 Al/Kaolin | 20 | runny | 2.9 | 3.4 | 76 (4) | 54 (8) | 67 (9) | 53 (8) |
| N74P54 | 2000 Al/Kaolin | 70 | thick | 3.4 | 3.8 | 73 (6) | 41 (11) | 65 (5) | 43 (16) |
| N74P56 | 2000 Al/Kaolin | 85 | thick | 3.3 | 3.8 | 82 (4) | 55 (15) | 74 (2) | 53 (13) |
| N74P58 | 2000 Al/Kaolin | 67 | thick | 3.4 | 3.7 | 68 (1) | 40 (8) | 61 (3) | 39 (7) |
| N74P60 | 2000 Al/Kaolin | 77 | thick | 3.4 | 4.0 | 78 (4) | 54 (10 | 73 (3) | 55 (9) |
| N74P62 | 2000 Al/Kaolin | 73 | thick | 3.9 | 4.1 | 65 (5) | 32 (11) | 62 (3) | 32 (11) |
| N74P70 | 2000 Al/Kaolin | 52 | fair | 3.8 | 4.4 | 80 (3) | 57 (1) | 70 (7) | 50 (4) |
| N74P72 | 2000 Al/Kaolin | 18 | runny | 3.0 | 3.4 | 72 (3) | 39 (10) | 70 (3) | 41 (10) |
| N74P74 | 2000 Al/Kaolin | 49 | good | 3.8 | 4.0 | 78 (4) | 42 (10) | 71 (3) | 37 (5) |
| N74P76 | 2000 Al/Kaolin | 42 | good | 3.9 | 4.0 | 69 (17) | 45 (11) | 64 (15) | 44 (9) |
| N74P78 | 2000 Al/Kaolin | 8 | runny | 3.7 | 4.0 | 70 (5) | 41 (13) | 65 (5) | 36 (9) |
| N74P80 | 2000 Al/Kaolin | 26 | good | 3.8 | 3.9 | 70 (1) | 33 (6) | 66 (1) | 32 (6) |
| N74P86 | 2000 Al/Silica | 3 | runny | 3.7 | 4.0 | 72 (7) | 46 (3) | 64 (8) | 44 (5) |
| N74P88 | 2000 Al/Silica | 32 | good | 3.6 | 3.9 | 72 (4) | 45 (8) | 67 (1) | 46 (3) |
| N74P90 | 2000 Al/Kaolin | 16 | separ. | 3.8 | 4.0 | 75 (3) | 52 (8) | 68 (4) | 51 (7) |
| N74P92 | 2000 Al/Kaolin | 38 | good | 3.8 | 4.0 | 79 (4) | 54 (11) | 74 (2) | 54 (10) |
| N74P94 | 2000 Al/Kaolin | 34 | fair | 3.8 | 4.0 | 76 (5) | 47 (12) | 71 (5) | 45 (12) |
| N74P96 | 2000 Al/Kaolin | 14 | separ. | 3.8 | 4.0 | 81 (4) | 58 (9) | 73 (3) | 55 (7) |
| N74P98 | 2000 Al/Kaolin | 34 | good | 3.8 | 4.0 | 70 (2) | 36 (4) | 64 (1) | 39 (6) |

TABLE 2-continued

| DENTIFRICE CODE | DENTIFRICE DESCRIPTION | BROOKFIELD VISCOSITY 10 RPM VISUAL | | DENTIFRICE pH | | ENAMEL SOLUBILITY REDUCTION (%)* | | | |
|---|---|---|---|---|---|---|---|---|---|
| | | | | | | PHOSPHORUS | | CALCIUM | |
| | | | | PASTE | SLURRY | 1 PTD | 4 PTD | 1 PTD | 4 PTD |
| N74P100 | 2000 Al/Kaolin | 15 | runny | 3.8 | 4.1 | 72 (7) | 44 (8) | 70 (5) | 43 (9) |
| | | | | | | 76 (7) | 51 (12) | 69 (7) | 48 (12) |
| N74P108 | 2000 Al/Kaolin | 39 | good | 3.8 | 4.0 | 67 (5) | 28 (11) | 64 (5) | 29 (12) |
| N74P110 | 2000 Al/Kaolin | 27 | good | 3.8 | 4.0 | 80 (8) | 50 (13) | 74 (6) | 48 (14) |
| N74P112 | 4000 Al/Kaolin | 15 | runny | 3.7 | 3.8 | 67 (10) | 42 (13) | 61 (9) | 40 (13) |
| | | | | | | 70 (7) | 38 (14) | 64 (2) | 38 (13) |
| N74P114 | 2000 Al/Silica | 30 | good | 3.8 | 4.0 | 67 (8) | 31 (15) | 63 (9) | 37 (15) |
| N74P118 | 2000 Al/Kaolin | 55 | fair | 3.8 | 4.0 | 78 (3) | 53 (3) | 76 (3) | 52 (4) |
| N74P120 | 2000 Al/Kaolin | 28 | good | 3.8 | 4.0 | 71 (4) | 34 (20) | 69 (5) | 44 (22) |
| N74P122 | 2000 Al/Kaolin | 16 | good | 3.7 | 4.0 | 75 (2) | 46 (16) | 69 (4) | 42 (16) |
| N74P126 | no Al/Kaolin | 33 | good | 5.4 | 5.6 | 2 (23) | −5 (17) | 7 (18) | 0 (10) |
| N74P145 | 1500 Al/Kaolin | 9 | fair | 3.7 | 3.9 | 79 (4) | 60 (13) | 76 (6) | 59 (15) |
| N74P146 | 1000 Al/Kaolin | 9 | fair | 3.7 | 3.9 | 78 (3) | 60 (7) | 77 (3) | 60 (7) |
| N74P147 | 500 Al/Kaolin | 26 | good | 3.7 | 3.9 | 58 (17) | 28 (18) | 55 (18) | 24 (19) |
| COLGATE | 1000 MFP | 22 | good | 7.2 | 7.2 | 32 (7) | 6 (7) | 29 (211) | 11 (11) |
| AIM | 1000 MFP | — | — | 6.3 | 6.3 | 24 (10) | 0 (11) | 23 (10) | −2 (9) |
| AIM EXTRA | 1500 MFP | — | — | 6.3 | 6.3 | 36 (11) | 18 (12) | 34 (11) | 17 (10) |
| Water | Neg. Control | — | — | — | 6.6 | 13 (21) | −2 (22) | 2 (9) | −6 (7) |
| 2000 Al | Pos. Control | — | — | — | 3.8 | 67 (4) | 33 (11) | 60 (3) | 36 (7) |

*Mean value (+ standard deviation), n = 3

Viscosity measurements were conducted using a Brookfield viscometer equipped with the F t-bar spindle. Viscosity scores for all of the dentifrices at the 10 rpm shear rate are recorded in Table 2 as well as a visual assessment of dentifrice viscosity when the dentifrice is extruded from a tube. Proper viscosity is essential for tube extrudability, adherence to the toothbrush, and dispersability in the mouth.

The cariostatic activity of the dentifrice formulations were determined by enamel solubility reduction (ESR) investigations. The ESR data in Table 2 demonstrate that all of the systems containing 2000 ppm aluminum were highly active and produced 1st PTD ESR scores of approximately 70% and 4th PTD ESR scores of about 40%. Since the ESR scores of the aluminum-containing dentifrices were equivalent to the positive control, a 2000 ppm aluminum solution containing no added ingredients, it can be assumed that all the ingredients in the exemplified dentifrice formulations are aluminum ion compatible. For comparison, ESR data for three commercial fluoride dentifrices (Colgate, Aim, and Aim Extra Strength) are also included in Table 2. The data also reflect significant cariostatic superiority of aluminum dentifrices over current fluoride dentifrice products.

The present improvements are particularly adapted for use in the large-scale formulation of aluminum dentifrices having the formulations specified in Table 3.

TABLE 3

Aluminum Dentifrice

| Component | Function | Quantitative Composition |
|---|---|---|
| Kaopolite 1147 (Calcined Aluminum Silicate) | Abrasive | 27–31% |
| Titanium Dioxide | Whitener | 2% |
| Glycerin, 96%, USP | Humectant | 16–18% |
| Sorbitol, 70%, (Sorbo), USP | Humectant | 12–15% |
| Propyl paraben, UPS | Preservative | 0.05% |
| Methyl paraben, USP | Preservative | 0.15% |
| Zeosyl 200 (Precipitated Amorphous Silica) | Binder | 3–4% |
| Natrosol 250 MR (Hydroxyethyl Cellulose) | Binder | 0.5–1.0% |
| Pluronic F127 (Block Copolymer) | Surfactant | 8–10% |
| Pluronic L64 (Block Copolymer) | Emulsifier | 0.7–0.9% |
| Sodium Hydroxide (33.3%) | pH Adjuster | 0.25–0.30% |

TABLE 3-continued

Aluminum Dentifrice

| Component | Function | Quantitative Composition |
|---|---|---|
| Intarome mint I-1376 | Flavor | 1.0–1.5% |
| Givaudan strawberry 74696-33 | Flavor | 0.4–0.6% |
| H&R mint 757082 | Flavor | 1.0–1.5% |
| Menthol | Flavor | 0.4–0.6% |
| Anethole | Flavor | 0.1–0.2% |
| Sodium Saccharin (85%), NF | Sweetener | 0.5–0.8% |
| Aluminum Potassium Sulfate dodecahydrate (Food Grade) | Anticaries Agent | 1.77% |
| Deionized Water | | Q.S. |
| | | 100.000 |

An aluminum dentifrice having the following formula was prepared for clinical trials using the outlined manufacturing procedure.

| ALUMINUM DENTIFRICE INGREDIENTS LIST | |
|---|---|
| INGREDIENT | MASS (kg) |
| Potassium Alum | 10.0 |
| Sodium Saccharin | 4.0 |
| Sorbo (70%) USP | 75.0 |
| Sodium Hydrox. 33% | 1.67 |
| Natrosol 250 MR | 6.67 |
| Glycerine USP | 100.0 |
| Pluronic F127 | 53.33 |
| Methyl Paraben | 1.0 |
| Propyl Paraben | 0.33 |
| Kaopolite 1147 | 166.67 |
| Zeozyl 200 | 20.0 |
| Titanium Dioxide | 13.33 |
| Pluronic L64 | 6.67 |
| Flavor | 6.67 |

Equipment

1—Nauta MBX Mixer, stainless steel
3—Auxiliary stainless steel mixing vessels

Process

1. Natrosol-Aluminum Intermediate
   a. Charge the deionized water to an auxiliary mixer.
   b. Begin agitation and charge the potassium alum. Agitate until dissolved (45–60 minutes).

c. Add in sodium saccharin. Agitate until dissolved (3-5 minutes).
d. Charge the sorbo and agitate until mixed (3-5 minutes).
e. Slowly add the sodium hydroxide with rapid stirring until solution is clear (10-15 minutes).
f. Slowly sift in the Natrosol 250 MR binder with rapid agitation. Mix at moderate speed until the Natrosol is completely hydrated (approximately 2 hours).
g. Take a representative sample and check the pH. It should be approximately 3.5

2. Pluronic-Glycerin Intermediate
a. Charge the glycerin to an auxiliary mixer heated at 100° C.
b. Start moderate agitation and add the methyl and propyl parabens. Agitate until dissolved (30-45 minutes).
c. Add the Pluronic F127 and agitate until it totally disperses into a uniform mass free of lumps (30-45 minutes).
d. Maintain the mixture at temperature until charged to the Nauta mixer.

3. Flavor Emulsion Intermediate
a. Charge the Pluronic L64 to an auxiliary mixer.
b. Start the mixer with moderate agitation. Add the flavors and agitate until evenly dispersed.

4. Finished Product
a. Charge the Natrosol-Aluminum Intermediate to Nauta mixer and start mixing screw with downward high speed agitation.
b. Add the Pluronic-Glycerin Intermediate and start lump breakers.
c. Add the Zeosyl 200 binder and agitate to uniformity.
d. Start upward screw high speed agitation and sift in titanium dioxide and the abrasive. NOTE: The abrasive will lump if poured rapidly. Use dust masks to avoid inhalation of abrasive.
e. Seal the mixer and draw a vacuum of 28" Hg. or more. Turn cooling water on and maintain a 70°-80° F. range throughout the remainder of the batch. Mix for 30 minutes with downward high speed. Mix for 20 additional minutes with upward high speed.
f. Release the vacuum, stop agitation and layer the Flavor Emulsion Intermediate on top.
g. Seal the mixer and pull a vacuum of 28" Hg. or more. Agitate at downward high speed for ten minutes then upward high speed until uniform (15 minutes).
h. Take a sample and measure specific gravity and pH.
i. Take a representative sample for retain and pump batch to storage through a 60 mesh strainer.
j. Charge the product into clean, plastic dentifrice tubes (3, 5 or 7 oz.).
k. Heat seal open end of tube and imprint lot number on the closure.

Although the invention has been described in detail with reference to certain preferred embodiments, variations and modifications exist within the scope and spirit of the invention as described in the following claims.

What is claimed:

1. In a method for manufacturing a palatable, aluminum-based anticariogenic composition comprising a water-soluble aluminum salt, water, humectant, flavor oil, surfactant, and sweetener in a blended emulsion, the improvement which comprises the steps of
preparing an aqueous solution comprising the aluminum salt and at least a portion of the humectant in a minimum amount of water,
adjusting the pH of the solution to about 3.2 to about 4.0 by addition of a food-acceptable base, and thereafter
blending the pH-adjusted aqueous solution with the remaining composition ingredients.

2. The improvement of claim 1 wherein the anticariogenic composition further comprises an aluminum-compatible cellulosic binder, and the binder is added to the aqueous solution after pH adjustment and before blending same with the remaining composition ingredients.

3. The improvement of claim 1 further comprising the steps of blending a second portion of the humectant with at least one surfactant component to form an organic premix and blending the organic premix with the pH-adjusted aqueous solution.

4. The improvement of claim 3 wherein the organic premix and the aqueous solution are blended under vacuum.

5. The improvement of claim 2 further comprising the steps of blending a second portion of the humectant with at least one surfactant component to form an organic premix and blending the organic premix with the aqueous solution.

6. The improvement of claim 5 wherein the organic premix and the aqueous solution are blended under vacuum.

7. The improvement of claim 5 wherein the anticariogenic composition further comprises an aluminum-compatible abrasive and the improvement further comprises the step of mixing the abrasive into the blend of the organic premix and the aqueous solution.

8. The improvement of claim 6 wherein the anticariogenic composition further comprises an aluminum-compatible abrasive and the improvement further comprises the step of mixing the abrasive into the blend into the organic premix and the aqueous solution.

9. The improvement of claim 1 wherein the pH of the aluminum salt/humectant solution is adjusted to about 3.5 to about 3.9.

10. The improvement of claim 1 wherein the pH of the aluminum salt/humectant solution is adjusted to about 3.7 to about 3.9 with sodium hydroxide.

11. The improvement of claim 1 further comprising the step of pre-blending the flavor oil component with a portion of at least one surfactant component to form a flavor/surfactant premix and thereafter blending the premix with the aluminum salt/humectant solution and the remaining composition ingredients.

12. The improvement of claim 6 further comprising the step of pre-blending the flavor oil component with a portion of at least one surfactant component to form a flavor oil/surfactant premix and thereafter blending the premix with the remaining composition ingredients.

13. The improvement of claim 7 further comprising the step of pre-blending the flavor oil component with a portion of at least one surfactant component to form a flavor/surfactant premix and thereafter blending the premix with the aluminum salt/humectant solution and the remaining composition ingredients.

14. The improvement of claim 8 further comprising the step of pre-blending the flavor oil component with a portion of at least one surfactant component to form a flavor oil/surfactant premix and thereafter blending the premix with the remaining composition ingredients.

15. A method for manufacturing a palatable, aluminum-based anticariogenic composition in gel or paste form comprising a water-soluble aluminum salt, water, humectant, flavor oil, surfactants, cellulosic binder, abrasive and sweeteners, the method comprising the steps of preparing a solution comprising the aluminum salt and at least a portion of the humectant in a minimum amount of water, adjusting the pH of the solution to about 3.5 to about 3.9 by addition of a food-acceptable base, blending the cellulosic binder into the pH-adjusted aqueous solution to hydrate said binder, pre-blending a second portion of the humectant with at least one surfactant component to form an organic premix and thereafter blending the organic premix with the aqueous solution, pre-blending the flavor oil component with a portion of at least one surfactant component to form a flavor oil/surfactant premix and blending the flavor oil/surfactant premix and the abrasive component with the blended mixture of the organic premix and the aqueous aluminum/humectant solution.

16. The method of claim 15 where at least the last step of blending the flavor oil/surfactant premix with the abrasive and the other premixed ingredients is carried out under vacuum to remove and prevent incorporation of air in the mix.

* * * * *